(12) United States Patent
Fremy

(10) Patent No.: US 6,743,951 B2
(45) Date of Patent: Jun. 1, 2004

(54) COMPOSITIONS BASED ON DIMETHYL DISULPHIDE WITH A MASKED SMELL

(75) Inventor: Georges Fremy, OS-Marsillon (FR)

(73) Assignee: Elf Atochem S.A., Puteaux (FR)

( * ) Notice: Subject to any disclaimer, the term of this patent is extended or adjusted under 35 U.S.C. 154(b) by 0 days.

(21) Appl. No.: 10/043,282

(22) Filed: Jan. 14, 2002

(65) Prior Publication Data

US 2002/0156326 A1 Oct. 24, 2002

Related U.S. Application Data

(63) Continuation of application No. 09/350,994, filed on Jul. 12, 1999, now abandoned.

(30) Foreign Application Priority Data

Jul. 31, 1998 (FR) .............................. 98 09864

(51) Int. Cl.⁷ ............................................. C07C 321/14
(52) U.S. Cl. ...................................................... 568/21
(58) Field of Search ..................... 568/21, 25

(56) References Cited

U.S. PATENT DOCUMENTS

| 3,647,481 A | * | 3/1972 | Brodnitz et al. | |
| 3,764,709 A | * | 10/1973 | Galetto | |
| 4,355,183 A | * | 10/1982 | Nash et al. | 568/19 |
| 5,218,147 A | | 6/1993 | Shaw | |
| 5,312,993 A | * | 5/1994 | Arretz | 568/26 |
| 5,559,271 A | * | 9/1996 | Shaw | 568/21 |
| 6,114,586 A | | 9/2000 | Devaux et al. | 568/21 |
| 6,362,374 B1 | | 3/2002 | Forester et al. | 568/21 |

FOREIGN PATENT DOCUMENTS

EP 446109 9/1991

OTHER PUBLICATIONS

Alrich Chemical Catalogue p. 985 1996.*
International Search Report dated Apr. 7, 1999.
Aldrich–Catalogue Handbook of Fine Chemicals, 1996, p. 985.

* cited by examiner

*Primary Examiner*—Jean F. Vollano
(74) *Attorney, Agent, or Firm*—Smith, Gambrell & Russell, LLP

(57) ABSTRACT

A composition based on dimethyl disulphide (DMDS) with a masked smell according to the invention comprises, by weight, at least 95% of DMDS, less than 500 ppm of methyl mercaptan, less than 100 ppm of dimethyl sulphide and up to 1% of at least one odor-masking agent.

12 Claims, 2 Drawing Sheets

COMPOSITIONS BASED ON DIMETHYL DISULPHIDE WITH A MASKED SMELL

The present application is a continuation of Ser. No. 09/350,994, filed Jul. 12, 1999, now abandoned, which prior application is incorporated herein by reference.

FIELD OF THE INVENTION

The present invention relates to the field of organic sulphides and more particularly that of dimethyl disulphide.

BACKGROUND OF THE INVENTION

Dimethyl disulphide (DMDS) has a strong and aggressive smell due in part to the presence of highly odorous impurities and in part to the garlicky and ethereal smell intrinsic to DMDS. This strong smell hinders the increased growth of this product in applications such as the sulphurization of catalysts or as loading additive for steam cracking. In comparison with other products used in these applications, such as tert-alkyl polysulphides, DMDS exhibits numerous advantages, in particular a high sulphur content (68%) and non-coking degradation products ($CH_4$, $H_2S$) Furthermore, in these applications, DMDS results in generally superior performances to other products, such as tert-alkyl polysulphides. However, these other products have markedly lower odorous levels which, for this reason, make them easier to handle in comparison with DMDS.

A particularly efficient and economical method, among the methods for the synthesis of DMDS, is the oxidation of methyl mercaptan by sulphur according to the reaction:

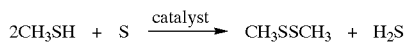

This oxidation of methyl mercaptan by sulphur, catalysed by organic or inorganic, homogeneous or heterogeneous, basic agents under batchwise or continuous conditions, is accompanied by a release of hydrogen sulphide and of dimethyl polysulphides ($CH_3S_xCH_3$) with a sulphur rank x of greater than 2. In order to manufacture DMDS according to this process with high yields and a limited production of DMPS (dimethyl polysulphides with a rank greater than 2), European Patent 0,446,109, the contents of which are incorporated here by reference, discloses a preparation process comprising two reaction regions interrupted by an intermediate degassing region and followed by a distillation region. Although giving a good performance in terms of yield and selectivity for DMDS, it turns out that this process results in a not insignificant amount of methyl mercaptan (approximately 4000 ppm) and a very small amount of dimethyl sulphide (approximately 300 ppm), originating from the methyl mercaptan used or produced during the synthesis of DMDS, being left in the finished product. The result of these volatile impurities is that they render the smell of the DMDS very unpleasant and aggressive and this strong smell is regarded as a significant cause of trouble during the handling of this product by users.

In order to mask the smell of organic polysulphides, U.S. Pat. No. 5,559,271 recommends adding a certain amount of masking product to them, such as, in particular, vanillin or ethyl vanillin. Although its general formula includes DMDS, this patent is more particularly targeted at the treatment of heavy polysulphides, such as, for example, di-t-nonyl pentasulphide. The application of this method to DMDS does not allow its nauseating and highly unpleasant smell to be masked.

It has now been found that, in the specific case of DMDS, the addition of an odour-masking agent is only effective if the DMDS used exhibits reduced contents of highly odorous volatile impurities, such as methyl mercaptan and dimethyl sulphide, and preferably comprises less than 200 ppm by weight of methyl mercaptan and less than 50 ppm by weight of dimethyl sulphide. It has also been found that the most effective odour-masking agents are not those mentioned in the abovementioned U.S. patent but those chosen from the esters corresponding to the general formula:

$$R^1CO_2R^2 \quad (I)$$

in which $R^1$ represents an optionally unsaturated, linear or branched hydrocarbon-comprising radical comprising from 1 to 4 carbon atoms and $R^2$ represents an optionally unsaturated, linear, branched or cyclic hydrocarbon-comprising radical comprising from 2 to 8 carbon atoms.

The subject-matter of the invention is therefore a DMDS-based composition, characterized in that it comprises, by weight, at least 95% of dimethyl disulphide, less than 500 ppm of methyl mercaptan (MM), less than 100 ppm of dimethyl sulphide (DMS) and up to 1% of at least one odour-masking agent, preferably an ester of general formula (I).

Any method known to a person skilled in the art for producing a DMDS with reduced contents of volatile impurities, such as MM and DMS, can be used in the context of the present invention. However, in the case of a DMDS comprising high contents of MM and DMS, a particularly preferred method consists of a distillative topping. This method exhibits the advantage of jointly removing MM and DMS, whereas the usual methods for smell reduction, generally based on removing residual mercaptans by specific reaction of a mercaptan functional group with a removal agent, such as a base or an alkene oxide in the presence of a base, are without effect on DMS present in DMDS.

The DMDS, thus topped, which preferably comprises less than 200 ppm of MM and less than 50 ppm of DMS, is used to prepare a composition according to the invention by simple addition of at least one odour-masking agent.

As one of the main advantages of DMDS in its applications is its high sulphur content (68%), an excessively high content of odour-masking agent in the composition would result in this sulphur assay being lowered and would decrease the advantage of this product in its main applications. The maximum content of odour-masking agent(s) is therefore set at 1% but this content is preferably between 0.1 and 0.5% and more particularly equal to approximately 0.2%.

Mention may be made, as illustrative but non-limiting examples of esters of general formula (I), of butyl acetate, isoamyl acetate, benzyl acetate, ethyl butyrate, propyl butyrate, butyl butyrate, 2-methylbutyl butyrate or isoamyl butyrate. Isoamyl acetate, 2-methylbutyl butyrate, isoamyl butyrate, benzyl acetate and the mixtures of these compounds are more particularly preferred. The esters (I) may or may not be used in combination with ortho-phthalates corresponding to the general formula:

in which the symbols $R^3$ and $R^4$, which are identical or different, each represent an optionally unsaturated, linear, branched or cyclic hydrocarbon-comprising radical comprising from 1 to 8 carbon atoms. Mention may more particularly be made, as non-limiting example of compound (II), of diethyl ortho-phthalate.

A typical composition of the present invention comprises, by weight:

| | |
|---|---|
| isoamyl acetate: | 0.1% |
| diethyl ortho-phthalate: | 0.1% |
| topped DMDS: | 99.8% |

Another typical composition of the present invention comprises, by weight:

| | |
|---|---|
| isoamyl acetate: | 0.05% |
| 2-methylbutyl butyrate: | 0.03% |
| benzyl acetate: | 0.02% |
| diethyl ortho-phthalate: | 0.1% |
| topped DMDS: | 99.8% |

The following examples illustrate the invention without limiting it.

EXAMPLE 1

Figure 1:
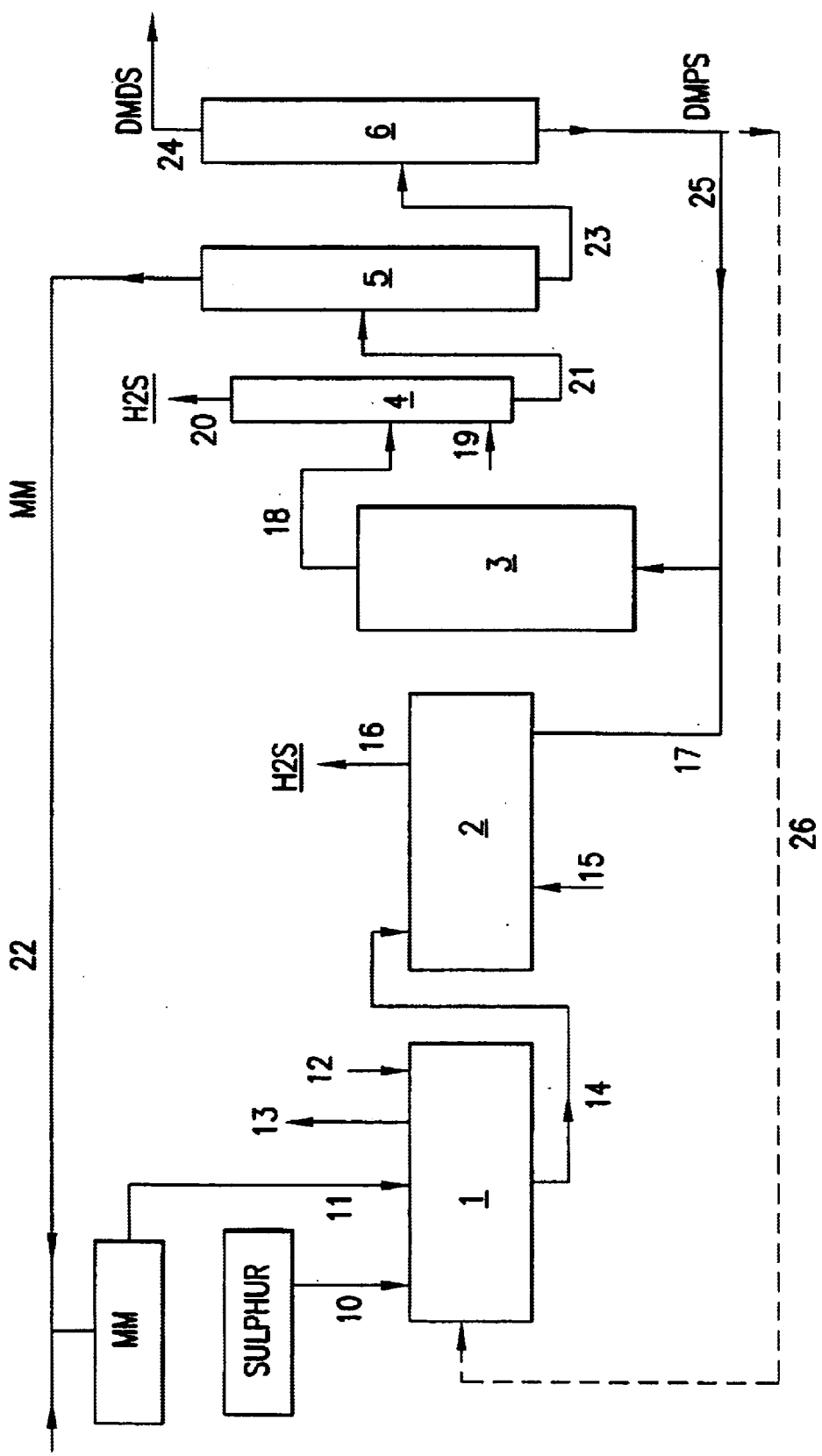
FIG. 1. shows a flow diagram of a plant for the synthesis of dimethyl disulfide.

Synthesis of Dimethyl Disulphide According to the Process Disclosed in Patent EP 0,446,109 a) Equipment: The appended FIG. 1 is a diagram of the plant used, combining two reactors (primary reactor 1 and finishing reactor 3). The primary reactor is a stirred reactor and the finishing reactor is a stationary-bed tubular reactor. A degassing system is positioned between these two reactors, this system being composed of a jacketed receptacle 2 equipped with a stirrer and surmounted by a cooled column which allows the methyl mercaptan, which can be carried away with the hydrogen sulphide, to be recondensed before being removed. This plant is completed by a pump, placed between the outlet of the degasser 2 and the inlet of the finishing reactor 3, which makes it possible to feed this reactor with liquid product treated in the degasser. A degassing column 4 serves to completely remove H$_2$S dissolved in the liquid exiting from the reactor 3. A distillation column 5 makes it possible to separate most of the excess methyl mercaptan for the purpose of recycling it via the pipe 22 to the reactor 1. The column 6 makes it possible to separate the residual dimethyl polysulphides (DMPS) for the purpose of recycling them in the reactor 3 or the reactor 1.

b) Procedure: Methyl mercaptan (MM) is introduced liquid into the reactor 1 under pressure via the pipe 11 with a flow rate of 960 g/h. Liquid sulphur is introduced into the reactor 1 via the pipe 10 with a flow rate of 160 g/h (MM/S=4 molar). The reactor 1 (reaction volume: 300 ml) contains 20 g of dry Amberlyst A21 resin. The operating pressure is maintained at 5.5 bar relative and the temperature at 40° C. The reaction mixture at the outlet of reactor 1 has the following composition by weight, excluding excess methyl mercaptan and excluding H$_2$S: DMDS 85%, DMPS 15%. This reaction mixture is then conveyed into the degasser 2 via the pipe 14 in order to be treated. After treatment, the mixture, freed from H$_2$S, is conveyed via the pipe 17 into the finishing reactor 3, which contains a charge of 94 g of dry A21 resin. The pressure in the reactor is 5.5 bar relative and the temperature 40° C. At the outlet of the reactor 3, the mixture has the following composition by weight, excluding H$_2$S and excluding excess methyl mercaptan: DMDS 98.5%, DMPS 1.5%. The mixture is then introduced via the pipe 18 into the degasser 4, in order to remove the H$_2$S which has formed in the reactor 3 during the retrogression of the dimethyl polysulphides by methyl mercaptan to give DMDS.

At the outlet of the degassing column 4, the mixture is introduced via the pipe 21 into the first distillation column 5, in order to remove virtually all the excess methyl mercaptan. This methyl mercaptan can be recycled via the pipe 22 to the introduction of the reactants into the reactor 1. At the outlet of the column 5, the mixture is conveyed via the pipe 23 into the second distillation column 6, where the DMPSs are removed at the column bottom via the pipe 25, in order optionally to be recycled in the reactor 3, or via the pipe 26, in order optionally to be recycled in the reactor 1.

The DMDS, finally collected at the top of the column 6 via the pipe 24 and known as A$_o$ for the olfactory tests described in the following examples, has the following composition by weight:

| | |
|---|---|
| DMDS: | 99.3% |
| DMPS: | 3000 ppm |
| MM: | 4000 ppm |
| DMS: | 300 ppm |

EXAMPLE 2

Purification of the Dimethyl Disulphide Prepared According to the Process Disclosed in Patent EP 0, 446,109

Figure 2:
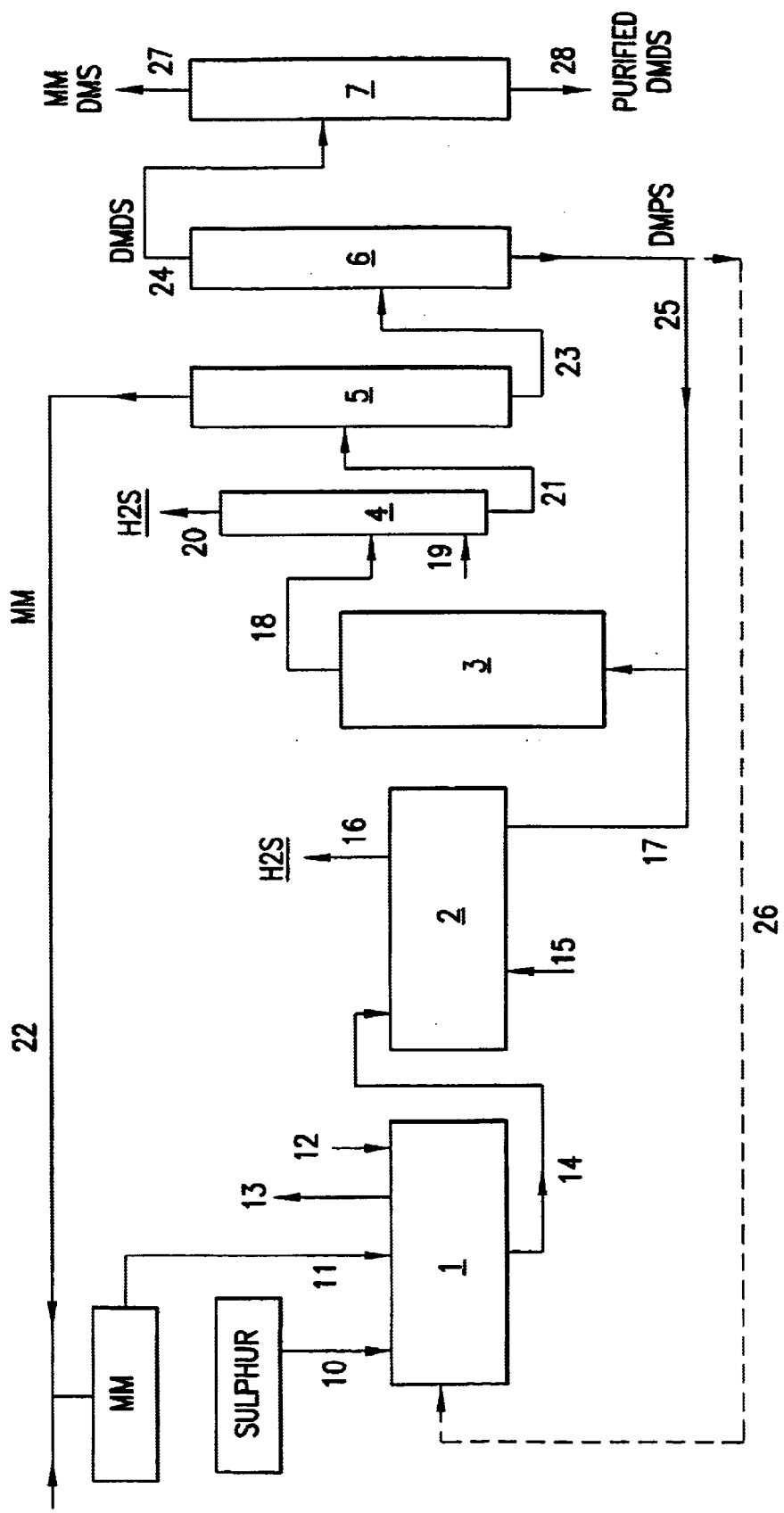
FIG. 2. shows a modified embodiment of the flow diagram of the plant according to FIG. 1.

The synthetic procedure is the same as that described in Example 1, except that the DMDS exiting from the column 6 via the pipe 24 is introduced into a third distillation column 7 (see diagram in the appended FIG. 2), where the volatile impurities, such as methyl mercaptan and dimethyl sulphide, are removed at the column top via the pipe 27. The DMDS collected at the column bottom via the pipe 28 has the following composition by weight:

| | |
|---|---|
| DMDS: | 99.7% |
| DMPS: | 3000 ppm |
| MM: | <100 ppm |
| DMS: | <50 ppm |

This purified DMDS, hereinafter known as B$_o$, and a DMDS sample A$_o$ prepared in Example 1 were subjected to an olfactory test. The 8 people invited to this test unanimously recognized a marked improvement in the smell of the B$_o$ DMDS in comparison with the A$_o$ DMDS but everyone also reported that a garlicky and ethereal smell remained in the B$_o$ DMDS.

EXAMPLE 3

2000 ppm by weight of vanillin (4-hydroxy-3-methoxybenzaldehyde) were added to 100 g of B$_o$ DMDS prepared in Example 2. The complete dissolution of the vanillin was observed after one hour at 25° C. The resulting sample was known as $B_1$.

EXAMPLE 4

The vanillin used in Example 3 was replaced by 2000 ppm of ethyl vanillin (3-ethoxy-4-hydroxybenzaldehyde). Its dissolution was observed after one hour at 25° C. The resulting sample was known as $B_2$.

Examples 5 and 6 illustrate the preparation of DMDS-based compositions with the smell masked by the preferred products of the present invention.

EXAMPLE 5

2000 ppm of a mixture composed by weight of 50% isoamyl acetate and 50% diethyl ortho-phthalate were added to 100 g of $B_o$ DMDS prepared in Example 2. As this mixture was liquid, dissolution was immediate at 25° C. The resulting sample was known as $B_3$.

EXAMPLE 6

The mixture used in Example 5 was replaced by 2000 ppm of a mixture having the following composition by weight:

| | |
|---|---|
| isoamyl acetate: | 25% |
| diethyl ortho-phthalate: | 50% |
| 2-methylbutyl butyrate: | 15% |
| benzyl acetate: | 10% |

The dissolution of this mixture in $B_o$ was immediate at 25° C. The resulting sample was known as $B_4$.

The samples $B_o$, $B_1$, $B_2$, $B_3$ and $B_4$ were subjected to a comparative olfactory test carried out by the panel of 8 people mentioned in Example 2. It was asked of these 8 people to attribute to the samples a note ranging from 0 to 5 according to their preference with respect to the smell, the note 0 being attributed to the least preferred smell, the note 5 to the most preferred smell and the notes 1, 2, 3 and 4 allowing them to classify the intermediate levels. The results are represented in the following table:

| Sample Person | $B_o$ | $B_1$ | $B_2$ | $B_3$ | $B_4$ |
|---|---|---|---|---|---|
| 1 | 0 | 2 | 3 | 4 | 5 |
| 2 | 1 | 2 | 4 | 3 | 5 |
| 3 | 0 | 3 | 2 | 4 | 5 |
| 4 | 0 | 2 | 3 | 4 | 5 |
| 5 | 0 | 3 | 2 | 4 | 5 |
| 6 | 0 | 2 | 3 | 4 | 5 |
| 7 | 1 | 2 | 4 | 3 | 5 |
| 8 | 1 | 2 | 3 | 5 | 4 |
| Note out of 40 | 3/40 | 18/40 | 24/40 | 31/40 | 39/40 |

It will be noticed that the smell of the compositions $B_1$, $B_2$, $B_3$ and $B_4$ is always preferred to that of $B_o$ and that the note obtained for $B_4$ is very close to the maximum possible (40). The members of the panel, in addition, specified that they preferred the "fruity" note of the compositions $B_3$ and $B_4$ to the "vanilla-garlicky" note of the compositions $B_1$ and $B_2$.

Comparative Examples 7 to 11 illustrate the need to remove most of the volatile impurities from the DMDS in order to observe a significant odour-masking effect.

EXAMPLE 7

Example 3 was repeated (masking agent: vanillin) but replacing 100 g of $B_o$ DMDS with 100 g of the non-topped DMDS $A_o$ prepared in Example 1. The resulting sample was known as $A_1$.

The 8 members of the panel compared the smell of $A_1$ with that of $B_o$ and everyone preferred the smell of $B_o$ (DMDS purified of its volatile impurities and without masking agent) to that of the composition $A_1$ based on unpurified DMDS and on vanillin.

EXAMPLE 8

The procedure of Example 7 was followed, vanillin being replaced by ethyl vanillin. The 8 people of the panel preferred the smell of the sample $B_o$ to that of the resulting sample ($A_2$).

EXAMPLE 9

The procedure of Example 7 was followed, vanillin being replaced by menthol. The smell of the sample $B_o$ was still preferred to that of the resulting sample ($A_3$).

EXAMPLE 10

The procedure of Example 7 was followed, vanillin being replaced by the mixture of masking products mentioned in Example 5. The resulting sample was known as $A_4$. The 8 people of the panel preferred the smell of $B_o$ to that of $A_4$.

EXAMPLE 11

The procedure of Example 7 was followed, vanillin being replaced by the mixture of masking products mentioned in Example 6. The resulting sample was known as $A_5$. The smell of the sample $B_o$ was still preferred to that of the sample $A_5$.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A dimethyl disulphide (DMDS) composition having a reduced content of highly odorous volatile impurities allowing a reduced amount of odor-masking agent, the composition comprising by weight: (i) at least 95% of DMDS, (ii) less than 500 ppm of the highly odorous volatile impurity methyl mercaptan, (iii) less than 100 ppm of the highly odorous volatile impurity dimethyl sulphide; and (iv) at least one odour-masking agent, present and in an amount of up to 1%.

2. Composition according to claim 1, comprising less than 200 ppm of methyl mercaptan and less than 50 ppm of dimethyl sulphide.

3. Composition according to claim 1 or 2, comprising from 0.1 to 0.5% of odour-masking agent(s).

4. A dimethyl disulphide (DMDS) composition comprising by weight:
   (i) at least 95% of DMDS,
   (ii) less than 500 ppm of the highly odorous volatile impurity methyl mercaptan,
   (iii) less than 100 ppm of the highly odorous volatile impurity dimethyl sulphide; and (iv) at least one odour-masking agent, present and in an amount of up to 1%; wherein
the at least one odour-masking agent is selected from the esters corresponding to the general formula:

$$R^1CO_2R^2 \quad (I)$$

wherein $R^1$ represents an optionally unsaturated, linear or branched hydrocarbon radical comprising from 1 to 4 carbon atoms and $R^2$ represents an optionally unsaturated, linear, branched or cyclic hydrocarbon radical comprising from 2 to 8 carbon atoms.

5. Composition according to claim 4, in which the odour-masking agent is chosen from the group consisting of isoamyl acetate, 2-methylbutyl butyrate, isoamyl butyrate, benzyl acetate and the mixtures of these compounds.

6. Composition according to claim 4 or 5, in which the ester of formula (I) is used in combination with an ortho-phthalate corresponding to the general formula:

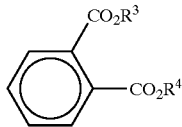
(II)

in which the symbols $R^3$ and $R^4$, which are identical or different, each represent an optionally unsaturated, linear, branched or cyclic hydrocarbon-comprising radical comprising from 1 to 8 carbon atoms.

7. Composition according to claim 6, in which the ortho-phthalate is diethyl ortho-phthalate.

8. Composition according to claim 7, comprising 0.1% of isoamyl acetate and 0.1% of diethyl ortho-phthalate.

9. Composition according to claim 7, comprising 0.05% of isoamyl acetate, 0.03% of 2-methylbutyl butyrate, 0.02% of benzyl acetate and 0.1% of diethyl ortho-phthalate.

10. Composition according to claim 3, wherein the amount of the at least one odor-masking agent is about 0.2%.

11. Composition based on dimethyl disulphide (DMDS), comprising by weight:

(i) at least 95% of DMDS;

(ii) less than 200 ppm of methyl mercaptan;

(iii) less than 50 ppm of dimethyl sulphide; and (iv) from 0.1 to 0.5% of at least one odor-masking agent selected from the esters of the formula:

$$R^1CO_2R^2 \quad (I)$$

in which $R^1$ represents an optionally unsaturated, linear or branched hydrocarbon radical containing from 1 to 4 carbon atoms and $R^2$ represents an optionally unsaturated, linear, branched or cyclic hydrocarbon radical containing from 2 to 8 carbon atoms.

12. Composition according to claim 11, wherein the composition further comprises an ortho-phthalate corresponding to the formula:

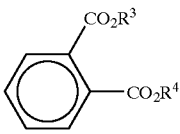
(II)

in which the symbols $R^3$ and $R^4$, which are identical or different, each represent an optionally unsaturated, linear, branched or cyclic hydrocarbon radical containing from 1 to 8 carbon atoms.

* * * * *